US010039632B2

(12) United States Patent
Lizzio

(10) Patent No.: US 10,039,632 B2
(45) Date of Patent: Aug. 7, 2018

(54) BIONIC MUSCLE

(71) Applicant: Clarus Technologies PTY LTD, Little Burra (AU)

(72) Inventor: Andrew Lizzio, Little Burra (AU)

(73) Assignee: Clarus Technologies Pty. Ltd., New South Wales (AU)

( * ) Notice: Subject to any disclaimer, the term of this patent is extended or adjusted under 35 U.S.C. 154(b) by 0 days.

(21) Appl. No.: 14/910,502

(22) PCT Filed: Aug. 2, 2014

(86) PCT No.: PCT/AU2014/050170
§ 371 (c)(1),
(2) Date: Feb. 5, 2016

(87) PCT Pub. No.: WO2015/017898
PCT Pub. Date: Feb. 12, 2015

(65) Prior Publication Data
US 2016/0184082 A1      Jun. 30, 2016

(30) Foreign Application Priority Data

Aug. 8, 2013    (AU) .............................. 2013902972

(51) Int. Cl.
*A61F 2/08* (2006.01)
*H01F 7/06* (2006.01)
(Continued)

(52) U.S. Cl.
CPC .............. *A61F 2/08* (2013.01); *H01F 7/066* (2013.01); *H01F 7/081* (2013.01);
(Continued)

(58) Field of Classification Search
CPC ............................. A61F 2/08; A61F 2/20036
(Continued)

(56) References Cited

U.S. PATENT DOCUMENTS 4,121,139 A    10/1978  Putt
4,516,102 A     5/1985  Rask
(Continued)

FOREIGN PATENT DOCUMENTS

CA        2100842        1/1995
CN     102653097 A       9/2012
(Continued)

OTHER PUBLICATIONS

PCT International Preliminary Report on Patentability in PCT/AU2014/050170, dated Feb. 9, 2016, 5 pages.
(Continued)

*Primary Examiner* — Suzette J Gherbi
(74) *Attorney, Agent, or Firm* — Servilla Whitney LLC

(57) ABSTRACT

The present invention provides an electromagnetic device comprising: a power circuit, and a contact initiated electromagnet having an electrical coil in operable connection with the power circuit, wherein one end of the electrical coil is directly connected to the power circuit and the other is connected to the magnetic core of the electromagnet such that, in use, the magnetic core performs the dual purposes of (i) focusing the electromagnetic field created by the coil and (ii) forms part of the electrical circuit that energizes the magnetic core of the electromagnet. Multiple electromagnetic devices may be combined to form a kinetic device capable of creating an electrically-based movement device that mimics the form and function of the skeletal muscle through the use of multiple contact initiated electromagnets held within elastic tubes.

21 Claims, 6 Drawing Sheets

(51) Int. Cl.
    *H01F 7/08* (2006.01)
    *A61F 2/48* (2006.01)
(52) U.S. Cl.
    CPC . *A61F 2002/0894* (2013.01); *A61F 2002/482* (2013.01); *A61F 2250/0001* (2013.01); *H01F 2007/086* (2013.01)
(58) Field of Classification Search
    USPC .......................................... 623/14.12–14.13
    See application file for complete search history.

(56) References Cited

U.S. PATENT DOCUMENTS

| | | | | |
|---|---|---|---|---|
| 8,517,963 | B2* | 8/2013 | Larson | A61B 17/1325 600/16 |
| 2010/0069994 | A1* | 3/2010 | Cauller | A61N 1/0536 607/46 |
| 2010/0217404 | A1 | 8/2010 | Kane | |
| 2010/0269689 | A1* | 10/2010 | Nakamura | F15B 15/103 92/92 |
| 2010/0331979 | A1* | 12/2010 | McDade | A61F 2/28 623/14.12 |
| 2011/0152967 | A1* | 6/2011 | Simon | A61N 1/40 607/45 |
| 2011/0251516 | A1* | 10/2011 | Doerr | A61B 5/07 600/562 |
| 2012/0229237 | A1 | 9/2012 | Zhao | |
| 2012/0323318 | A1* | 12/2012 | Yusuf | A61M 1/1053 623/3.11 |
| 2013/0030239 | A1* | 1/2013 | Weyh | A61N 2/006 600/14 |
| 2013/0030537 | A1* | 1/2013 | Linares | A61F 2/30771 623/18.11 |
| 2014/0005785 | A1* | 1/2014 | Massen | A61F 2/0036 623/14.13 |
| 2014/0357936 | A1* | 12/2014 | Simon | A61N 1/40 600/13 |
| 2015/0087892 | A1* | 3/2015 | Tourrel | A61N 1/375 600/25 |
| 2015/0257860 | A1* | 9/2015 | Andreen | A61C 13/235 433/189 |
| 2016/0017899 | A1* | 1/2016 | Yang | F15B 15/103 623/14.13 |
| 2017/0340243 | A1* | 11/2017 | Jain | A61B 5/076 |

FOREIGN PATENT DOCUMENTS

| | | |
|---|---|---|
| CN | 202952264 U | 5/2013 |
| WO | WO-97/27822 | 8/1997 |
| WO | WO-2006/129980 | 12/2006 |
| WO | 2013064108 A1 | 5/2013 |

OTHER PUBLICATIONS

PCT International Search Report in PCT/AU2014/050170, dated Sep. 22, 2014, 4 pages.
PCT International Written Opinion in PCT/AU2014/050170, dated Sep. 22, 2014, 4 pages.
Li, Jing, et al., Design and optimization of multi-class series-parallel linear electromagnetic array artificial muscle, *Biomed Motor Eng.* 21(1) 2014, 549-55.
Li, Jing, et al., Multi-object optimal design of electromagnetic artificial muscle structure, *2011 International Conference on TMEE, IEEE* 2011, 1152-1156.
Supplementary European Search Report in EP14835112 completed on Mar. 13, 2017, 1 page.

* cited by examiner

BIONIC MUSCLE

CROSS-REFERENCE TO RELATED APPLICATIONS

This is the United States National Phase entry of International Application No. PCT/AU2014/050170, filed Aug. 2, 2014, which claims priority to Australian Application No. 2013902972, filed Aug. 8, 2013, the disclosures of which are incorporated herein by reference in their entireties.

FIELD OF THE INVENTION

The present invention is in the field of bioengineering, and particularly in biomechanical engineering.

BACKGROUND TO THE INVENTION

As the global population ages and social structures change, our frail and disabled will need automated assistance to perform normal daily activities independently as support services become less available.

All current approaches to duplicating the skeletal muscle have taken the approach to replace a muscle mass with contrivances such as hydraulic/pneumatic ram-like devices, electric motor with gears/pulleys, pneumatic bladders. As a consequence, in order to achieve the necessary performance, these devices are bulky, require a sizeable power supply and are generally only capable of providing force between two anchor points along a straight line.

Furthermore current approaches typically require complex control systems to first sense and then control the amount of movement required to apply the required force to achieve the desired outcome.

Finally, current approaches are typically subject to environmental factors that will eventual impede and degrade their performance. They also require regular maintenance making them unsuitable for use in dangerous environments or for surgical implantation to replace a defective skeletal muscle.

It is an aspect of the present invention to overcome or ameliorate a problem of the prior art to provide personal assistive devices and systems that replicate skeletal muscles in both form and function. It is a further aspect of the present invention to provide a kinetic movement device configured to form a component for the construction or supplementation of organic or artificial movement systems. It is another aspect to provide a useful alternative to the prior art.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect, the present invention provides an electromagnetic device comprising:
  a power circuit, and
  a contact initiated electromagnet having an electrical coil in operable connection with the power circuit,
wherein one end of the electrical coil is directly connected to the power circuit and the other is connected to the magnetic core of the electromagnet such that, in use, the magnetic core performs the dual purposes of (i) focusing the electromagnetic field created by the coil and (ii) forms part of the electrical circuit that energizes the magnetic core of the electromagnet.

In second aspect the present invention comprises a kinetic device comprising two or more electromagnetic devices as described herein.

In one embodiment, the kinetic device is configured such that in use, when the electromagnet of a first electromagnetic device is energized, the magnetic field created magnetically attracts the electromagnet of an adjacent second electromagnetic device.

In one embodiment, the kinetic device is configured such that in use, when the electromagnet of the second electronic device makes electrical contact with the electromagnet of the first electromagnetic device, the electrical circuit for the electromagnet of the second electromagnetic device is closed and the electromagnet of the second electromagnetic device is energized to create a magnetic field.

In one embodiment, the two or more electromagnetic devices are disposed in series.

In one embodiment, the two or more electromagnetic devices are electrically connected in parallel.

In one embodiment, the kinetic device comprises a plurality of electromagnetic devices.

In a third aspect, the present invention provides a system for simulating the function of a partial or complete mammalian muscle, the system comprising one or more kinetic devices as described herein, the one or more kinetic devices encased in a biocompatible material.

In one embodiment, the biocompatible material is elastic.

In one embodiment, the biocompatible material forms a tubular cell, the tubular cell containing a plurality of kinetic devices.

In one embodiment, two or more electromagnetic devices within any one tubular cell are configured to be powered by the power circuit, with the amount of electrical energy applied is at least partially dependent on a mechanical force against which the system is operating.

In one embodiment, the system is configured such that adjacent tubular cells form one or more points of contact along the long axes.

In one embodiment, the tubular cells are configured such that the contact areas between two adjacent tubular cells is maximized over a range of angular displacements between the magnetic axis of the adjacent tubes.

In one embodiment, the electromagnetic devices within a tubular cell are, in their non-energized state, separated from one another along their magnetic axes by a distance that, when compared to the magnetic axial length of the tubular cell, creates a predetermined contraction ratio of the system when adjacent tubular cells are in contact.

In one embodiment, the system comprises two or more tubular cells configured to work mechanically in concert.

In one embodiment, the two or more tubular cells are encased by a biocompatible material to form a tubular cell grouping, In one embodiment the system comprises a non-conductive ferromagnetic fluid, the fluid at least partially surrounding one, most or all the kinetic devices.

In one embodiment, the biocompatible material is elastic.

In one embodiment, the tubular cells within a tubular cell grouping are displaced relative to each other.

In a fourth aspect, the present invention provides a method of treating a muscle disorder in an animal, the method comprising the step of implanting the kinetic device as described herein, or the system as described herein into an animal, wherein the kinetic device or system is directly or indirectly mechanically coupled to a skeletal component of the animal.

In one embodiment, the kinetic device or system is directly or indirectly electrically coupled to a neural component of the animal.

Also provided is a contact initiated electromagnet whereby one end of the electrical coil/windings is directly connected to the power circuit and the other is directly connected to the core of the electromagnet itself such that the core forms a dual purpose of focusing the electromagnetic field created by the coil/windings and forms part of electrical circuit that energizes the electromagnet itself.

Also provided is a bionic muscle mass comprised of multiple contact initiated electromagnets (hereinafter 'bionic muscle cells') specified above, encased in elastic tubes (which may be collectively referred to as 'bionic muscle fiber') where the bionic muscle cells within any one tube are powered in parallel but initiated in series dependant on the amount of electrical energy applied and the resistive force against which the bionic muscle is operating.

The bionic muscle mass specified above may have the bionic muscle cells are shaped so that the contact areas between two adjacent bionic muscle cells is maximized over a range of angular displacements between the magnetic axis of the adjacent bionic muscle cells.

The bionic muscle mass as specified above may have the bionic muscle cells within a bionic muscle fiber are, in their non-energized state, separated one from another along their magnetic axis by a distance that, when compared to the magnetic axial length of the bionic muscle cell, creates the desired contraction ratio of the bionic muscle when adjacent cells are in contact.

The bionic muscle mass as specified above may have its bionic muscle fibers grouped into groups of three or more bionic muscle fibers encased in an yet another elastic tube (referred to as 'bionic muscle groups') and the bionic muscle cells in one bionic muscle fiber in the bionic muscle group are displaced along the length of the bionic muscle fiber with respect to the bionic muscle cells in other bionic muscle fibers in the same bionic muscle group.

DETAILED DESCRIPTION OF THE INVENTION

Figure 1:
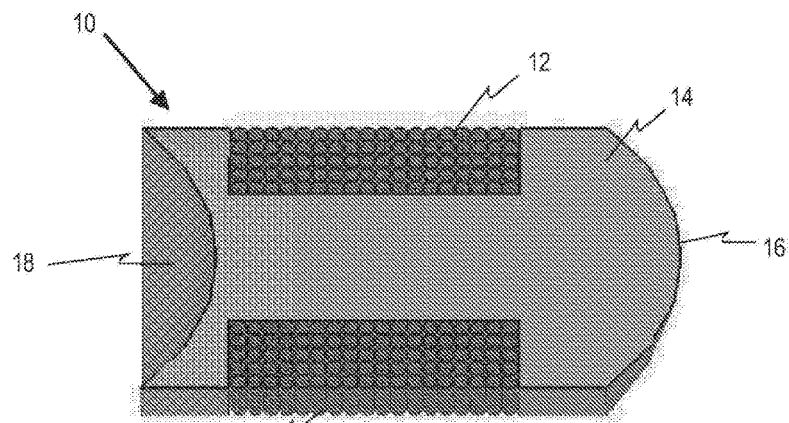
FIG. 1 is a perspective cut-away view of an example of the contact initiated electromagnet that forms the building block or bionic muscle cell for the present invention. This example takes the form of a simple 'dumbbell' design with matching convex and concave ends where the electrical circuit is completed by an electrical conductor running down the outside of the muscle fiber.
Figure 2:
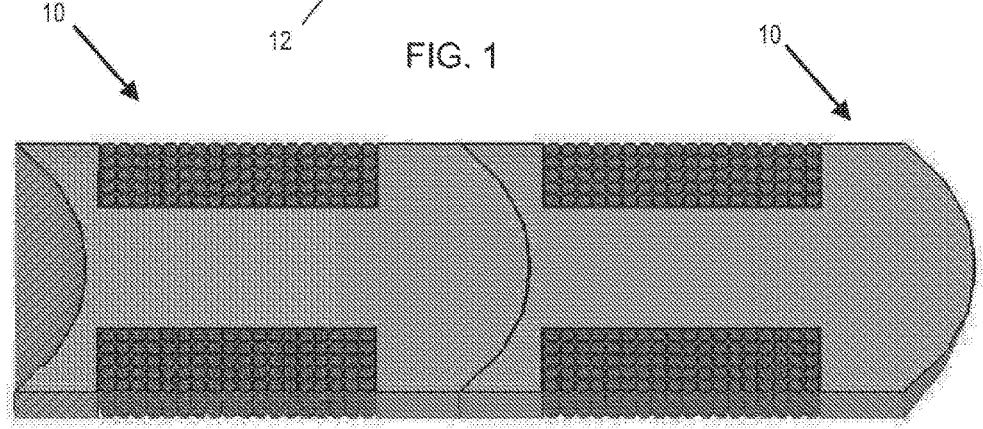
FIG. 2 is a perspective cut-away view showing how electrical contact is achieved between two adjoining bionic muscle cells when their axis are aligned.

After considering this description it is apparent to one skilled in the art how the invention is implemented in various alternative embodiments and alternative applications. However, although various embodiments of the present invention is described herein, it is understood that these embodiments are presented by way of example only, and not limitation. As such, this description of various alternative embodiments should not be construed to limit the scope or breadth of the present invention. Furthermore, statements of advantages or other aspects apply to specific exemplary embodiments, and not necessarily to all embodiments covered by the claims.

Throughout the description and the claims of this specification the word "comprise" and variations of the word, such as "comprising" and "comprises" is not intended to exclude other additives, components, integers or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may.

Rather than replace a muscle mass with a single device, the present invention replaces a single muscle mass with a plethora of very small devices that work together to duplicate the flexibility and performance of a skeletal muscle. In essence, an approach in one embodiment of this invention is to replace each muscle cell rather than the entire muscle mass, with an electromechanical equivalent.

The creation of the bionic muscle mass similarly mimics the elements of the biological skeletal muscle. That is: bionic muscle cells, in the form of miniature contact initiated electromagnets form the smallest building block of the bionic muscle; bionic muscle fibers, in the form of a linear series of spaced bionic muscle cells contained within a flexible sleeve; bionic muscle groups made up of three or more bionic muscle fibers encased in yet another flexible sleeve. The cells within each fiber are arranged so that they are in a staggered position one to another; and the bionic muscle mass itself which is comprised by a number of muscle groups. The number of bionic muscle groups that make up a bionic muscle mass will be proportional to the amount of force the bionic muscle group is to exert.

In some embodiments, the bionic muscle mass comprises a non-electroconductive ferrofluid that enhances magnetic field generation and also to conduct away waste heat.

The following are advantages of one, some, or all embodiments of the invention

BIOFEEDBACK: the bionic muscle has the ability to actively and instinctively respond to a greater opposing force by "letting go". This is achieved through the use of magnetic fields, where a magnetic field does not degrade or destruct when an external force exceeds the selected strength of the magnetic field (unlike rams, motors, worm drives, etc). This "letting go" attribute provides instant feedback to the bio or artificial controller, enabling an interaction process that is simple and real-time.

USABILITY: the bionic muscle has the ability to replicate muscles within the human body, thereby allowing humans to control artificial movement devices through natural interfaces. A full range of natural human movements can be achieved by creating an exoskeleton that mimics the placement and interaction of human muscles to a skeletal frame. Coupling this with a simplistic sensory feedback mechanism (see Biofeedback) creates a naturally usable solution. This usability can be extended by coupling the natural human interface to other natural non-human forms, for example birds for aeronautical control, fish for aqua nautical control, specialised digging animals for terraforming control, and agile movement animals for transportation.

ADAPTABILITY: the muscle invention has an increased ability to operate within a variety of environments through its ability to be sealed and ruggedized. The cellular design facilitates the use of a wide variety of construction materials, thereby adapting to safety, functional and operational demands for a given environment (e.g. within the human body, extreme temperatures, extreme pressures, excessive radiation, etc.).

SCALABILITY: the muscle invention has an increased ability to be scaled through its use of various construction materials (see Adaptability), thereby increasing the number of applications of use.

FLEXIBILITY: each muscle component consists of many independent cells, thereby allowing the muscle to extend force around other objects, or forgivingly comply with external forces (e.g. bend when pressed).

REDUNDANCY: each muscle component consists of many independent cells forming a network of functionality paths, thereby creating a system able to sustain a degree of damage.

AGILITY: each muscle component consists of many independent cells, thereby allowing cells to be maintained at a high frequency to quickly adapt to changing demands.

MAINTAINABILITY: each muscle component consists of many independent cells, thereby allowing selected cells to be replaced or enhanced without the constraints of other cells or components.

ROBUSTNESS: each muscle component consists of many independent cells forming a network of functionality paths, thereby allowing the muscle to reduce inoperable periods during operational demands by altering cells (see Maintainability) on inactive functionality paths.

CAPACITY: each muscle component has the ability to sustain a given level of continuous operation, including controlled surges of unsustainable operation (i.e. duty cycle). If the capacity of a muscle component is deemed sub-optimal, then it can be independently altered (see Maintainability and Robustness) to match the imposed operational demand within a timely period (see Agility).

AVAILABILITY: the muscle invention has an increased level of availability through its increased ability to sustain fault tolerance (see Accessibility and Redundancy), its increased ability to adapt (see Agility), and its increased level to be functionally operational over extended periods of time (see Maintainability, Robustness and Capacity).

The present invention will now be further described by way of the following non-limiting preferred embodiments.

PREFERRED EMBODIMENTS OF THE INVENTION

Bionic Muscle Cell

The key to the present invention of a bionic muscle is the development of a contact initiated electromagnet.

Unlike other electromagnets which have both ends of the electro-conductive coil connected directly to a power circuit, the electromagnet of the present invention only has one end of the electro-conductive coil connected directly to the power circuit. The other end of the coil is electrically terminated on the core of the electromagnet itself. Consequently, the core of the electromagnet performs the dual functions of (i) focusing the electromagnetic field created by the electro-conductive coil and (ii) forming part of the electrical circuit for the electromagnet.

The electrical circuit, which the contact initiated electromagnet of the present invention forms a part, is completed and the electromagnet is energized to create a magnetic field when the core of the electromagnetic makes electrical contact with another element of the electrical circuit.

The contact initiated electromagnet that is the key to the present invention of a bionic muscle has a variety of applications in its own right. However, when a series of these contact initiated electromagnets are arranged in series and powered in parallel within an elastic construct they form an electromagnetic equivalent of a normal biological muscle.

Once the first electromagnet in the series is energized, the magnetic field it creates magnetically attracts the next electromagnet in the series. Once the second electromagnet in the series makes electrical contact with the first electromagnet, the electrical circuit for the second electromagnet is closed and the second electromagnet becomes energized and creates its own magnetic field. The electromagnetic field created by the now energized second electromagnet now magnetically attracts the third magnetic in the series, ad nauseum.

FIG. 1 is but one example of the shape of such a bionic muscle cell 10 showing the windings 12 and core 14. Unlike existing electromagnets, the magnetic core of the electromagnet serves both a magnetic as well as an electric conductive function. The importance of this innovative feature will become apparent in the following description of the bionic muscle fiber.

Figure 3:
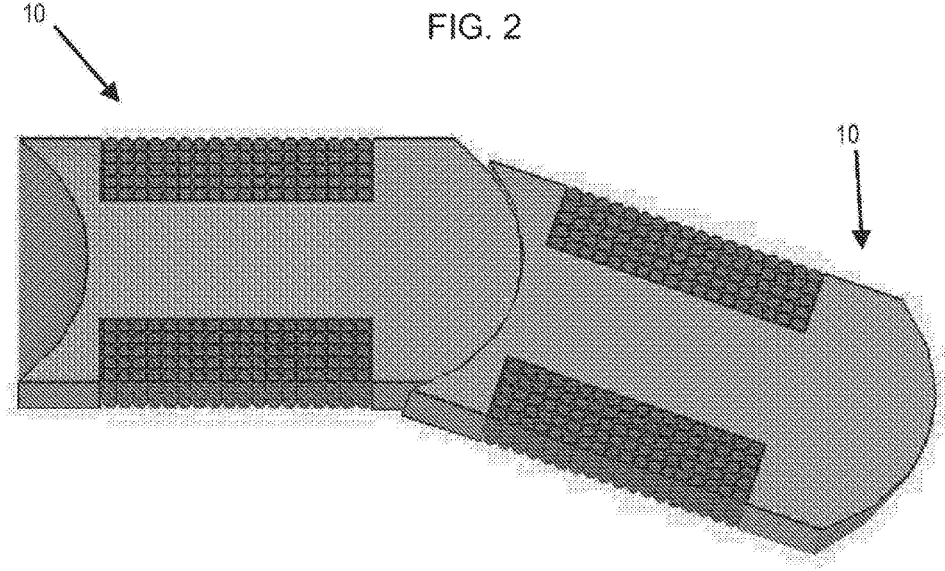
FIG. 3 is a perspective cut-away view showing how electrical contact is achieved between two adjoining bionic muscle cells when their axes are not aligned. This feature gives flexibility to the bionic muscle fiber and enables bionic muscle fibers, groups and masses to achieve contraction around corners and complex shapes.

The other innovative feature of the bionic muscle cell is its shape, having a convex first end 16 and a concave second end 18. Unlike normal electromagnets, the bionic muscle cell is shaped so that the area of contact is maximised over a range of angular displacements between contacting electromagnets (see FIG. 3). This feature ensures that electrical resistance is minimalized over a range of angular displacements.

The bionic muscle cell dumbbell is constructed from a single piece of magnetically soft material that has high magnetic permeability and is electrically conductive. Magnetic coils fill the inner of the dumbbell, with one end of the magnetic coil making a permanent electrical connection with the dumbbell shaped electromagnet core. The opposite end of the coil is permanently connected to the power source in parallel with all other muscle cells within the single muscle. The electrical circuit is closed when an inactive muscle cell electrically connects with an already energized, and hence electrically connected bionic muscle cell.

Bionic Muscle Fiber

While the bionic muscle cell is the building block of the bionic muscle mass, the bionic muscle fiber is the work engine of it.

Figure 4:
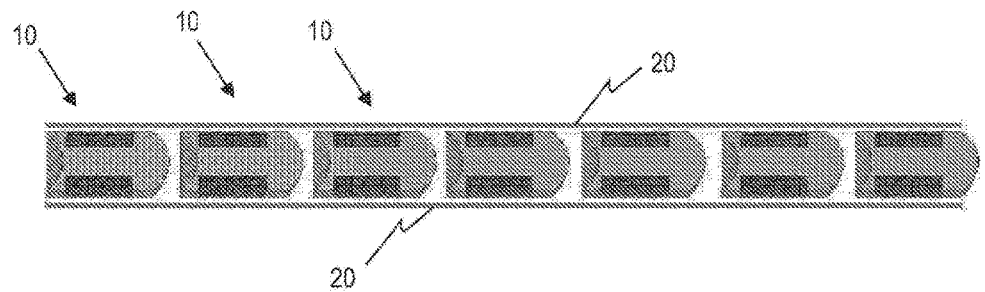
FIG. 4 is a perspective cut away view of a bionic muscle fiber using the electromagnet cells shown in FIG. 1 when none of the bionic muscle cells have been energized (i.e., the bionic muscle fiber is in its 'relaxed' state).

The bionic muscle fiber consists of a number of bionic cells 10 held in place within an elastic non-electro-conductive sheath 20. In its un-energized or 'relaxed' state (ie. no voltage applied) (see FIG. 4), each cell is separated from the next cell in the series by the desired contraction ratio. This separation provides that when fully energized, the muscle fiber will contract by the desired contraction ratio.

As voltage is applied to the first cell in the fiber, it creates a magnetic field that attracts the next cell in series, and by extension all magnetic cells in the series via the sheath that encases them all.

Figure 5:
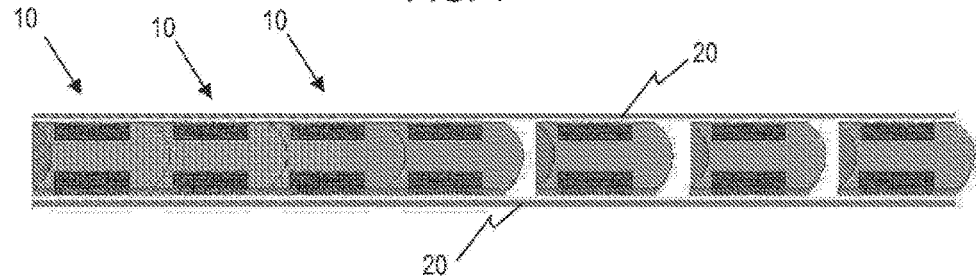
FIG. 5 is a perspective cut-away view of a bionic muscle fiber using the electromagnet cells shown in FIG. 1 when some of the bionic muscle cells have been energized (ie. the bionic muscle fiber is in a partially 'contracted' state).
Figure 9:
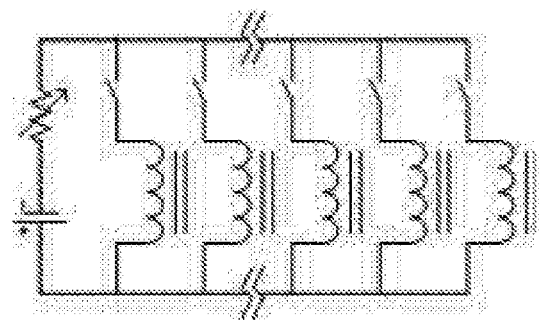
FIG. 9 is the electrical schematic for a bionic muscle fire showing how each bionic muscle cell is powered in parallel, but energized in serial.
Figure 10:
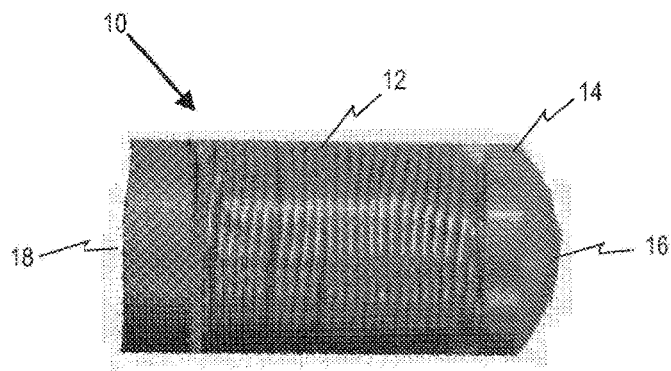
FIG. 10 is a photograph of a single kinetic device, of the type shown diagrammatically in FIG. 1.
Figure 11:
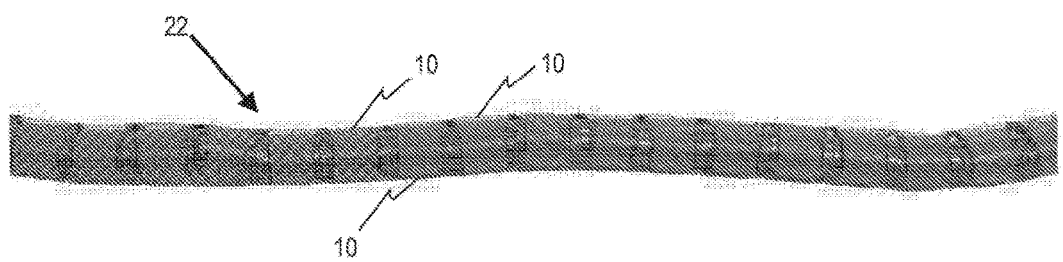
FIG. 11 is a photograph of a plurality of kinetic devices, of the type shown diagrammatically in FIGS. 4 and 5.
Figure 12:
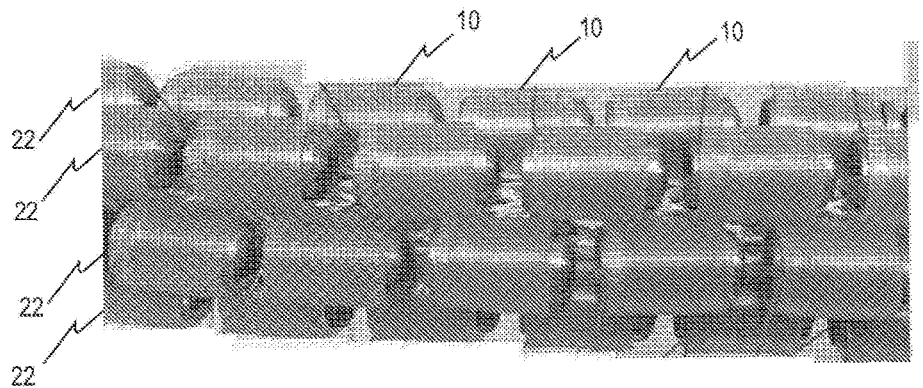
FIG. 12 is a photograph of a plurality of kinetic devices, of the type shown diagrammatically in FIGS. 6 and 7.
Figure 13:
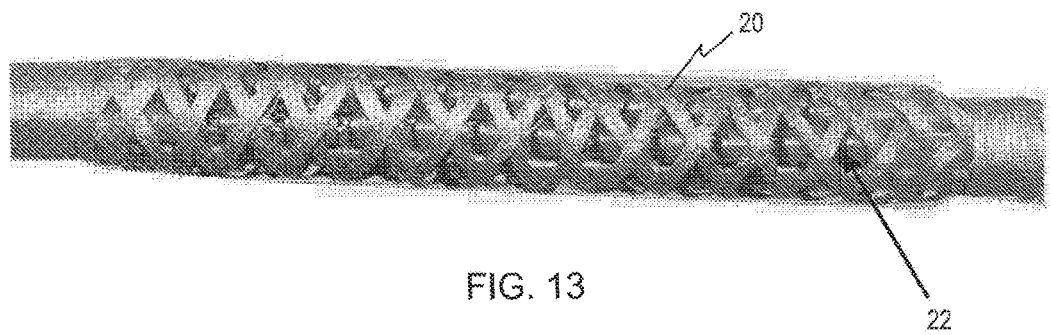
FIG. 13 is a photograph of a plurality of kinetic devices (of the type shown in FIG. 11) having an outer sheath.
Figure 14:
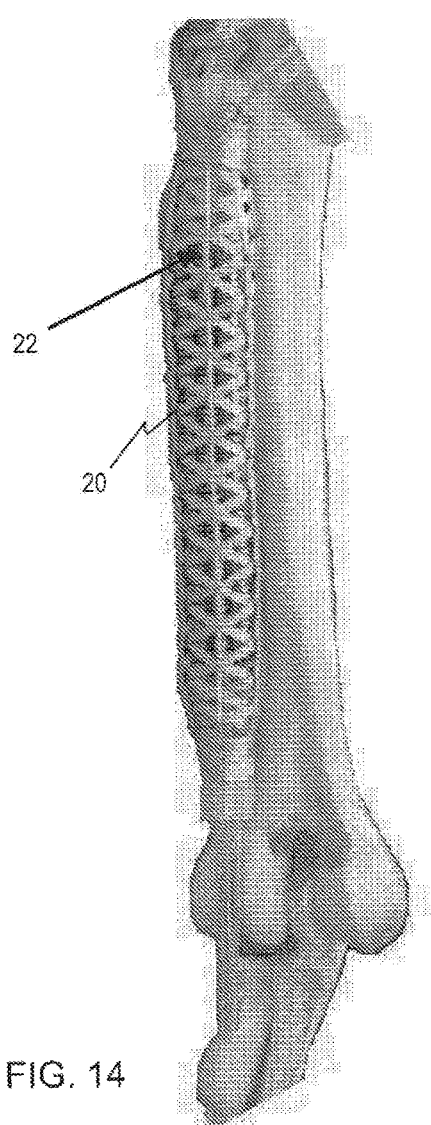
FIG. 14 is a representation of the sheathed device of FIG. 13 as applied to a mammalian bone in order to simulate a muscle.

Once the second cell makes contact with the first cell, the electrical circuit for the second cell is completed and it too creates a magnetic field that attracts the next (third) cell in the series (see FIG. 5). At the same time, since the cells are powered in parallel (see FIG. 9), the available voltage potential is now split between the two energized cells. The strength of the magnetic field generated by the second cell is therefore slightly weaker than the magnetic field generated by the first cell alone.

This process of attracting and energising cells in sequence continues until the combined resistive forces of the object the muscle fiber is work on is greater than the combined magnetic force produced by the energized muscle cells. In this manner, the electromagnetic bionic muscle fiber mimics the operation of the skeletal muscle which operates through a combination or electro-chemical and chemical-mechanical operations.

This novel approach eliminates the need for complex sensory and control systems because the movement is outcome driven rather than input-driven. That is, the operator applies more and more voltage, and hence force, until the outcome is achieved rather than first determining the movement required and controlling the servos or motors to achieve the same.

Bionic Muscle Group

Figure 6:
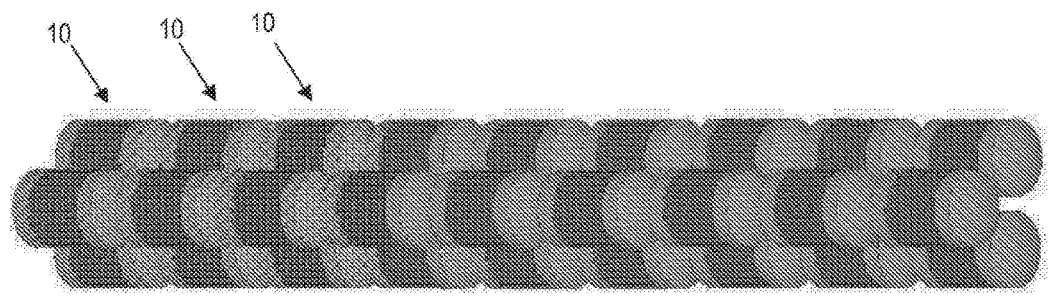
FIG. 6 is a perspective view of a three-fiber bionic muscle group in its un-energized or 'relaxed' state showing the staggered arrangement of bionic muscle cells. The staggered arrangement optimizes compression efficiency.
Figure 7:
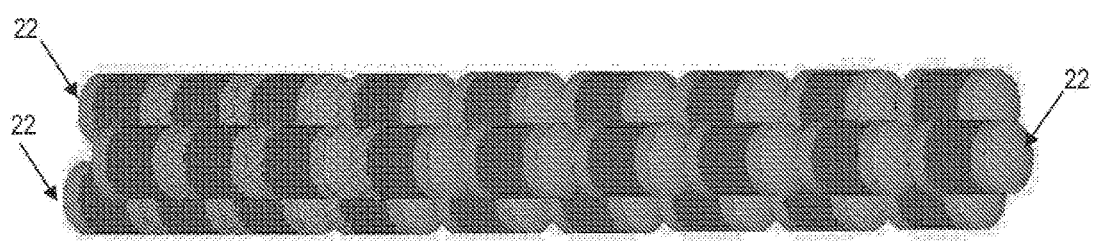
FIG. 7 is a persepctive view of a three-fiber bionic muscle group when some of the bionic muscle cells in each of the three bionic muscle fibers have been energized (ie. the bionic muscle group is in a partially 'contracted' state).

The bionic muscle group is a collection of three or more muscle fibers 22 within the same intermediate elastic non-electro-conductive sheath (see FIGS. 6 and 7).

The elastic non-electro-conductive sheath is used to keep the bionic muscle fibers together and to transfer contractive forces between fibers in the same group.

The number of bionic muscle fibers to a bionic muscle group will be governed by the magnetic force that can be generated by a single bionic muscle cell and the desired contraction ratio. The greater the desired contraction ratio, the greater the number of fibers and/or the greater the magnetic force that needs to be generated by a single cell.

The important feature of the bionic muscle group is that the bionic muscle cells in one bionic muscle fiber that forms part of the bionic muscle group are off-set along the length of the bionic muscle group to the bionic muscle cells of another fiber in the same bionic muscle group.

This feature means that at any one time during a contraction of the bionic muscle group, the next bionic muscle cell to make contact in one bionic muscle fiber may be at the full contraction ration separation, bionic muscle cells in the other bionic muscle fibers in the bionic muscle group are closer to one another. As a consequence, the amount of force required for the next bionic muscle cell to make contact, in any of the fibers in a group, is smaller than the force required within one fiber alone.

Furthermore, the increment of the contraction is equal to the ratio of the contraction divided by the number of bionic muscle fibers in the bionic muscle group. Consequently, the contraction is much smoother than would otherwise be the case if all the cells were aligned.

The fact that there is more than one fiber in a group also provides another feature of the present invention: namely, redundancy.

Without multiple muscle fibers the failure of a single bionic muscle cell would mean that the whole muscle would not work. This is because whilst a failed cell will still be attracted to the previous cell in the series it will not be activated to attract the next cell in the series.

However, because there are other fibers in the group, the fiber with the failed fiber will be forced to contract by the other fibers in the group. As a consequence, whilst the failed cell will not be activated, the next cell in that fiber will be forced into contact with the failed cell.

As a result, the next cell in that fiber can be activated and the remainder of the fiber with the failed cell will continue to work regardless.

In this construct, even with a failed cell, the muscle group will continue to work, albeit with a slight pause or 'sticking' point in the contraction.

Bionic Muscle Mass

Where the bionic muscle cell is the building block and the bionic muscle fiber is the work engine, the bionic muscle mass is the powerhouse.

Figure 8:
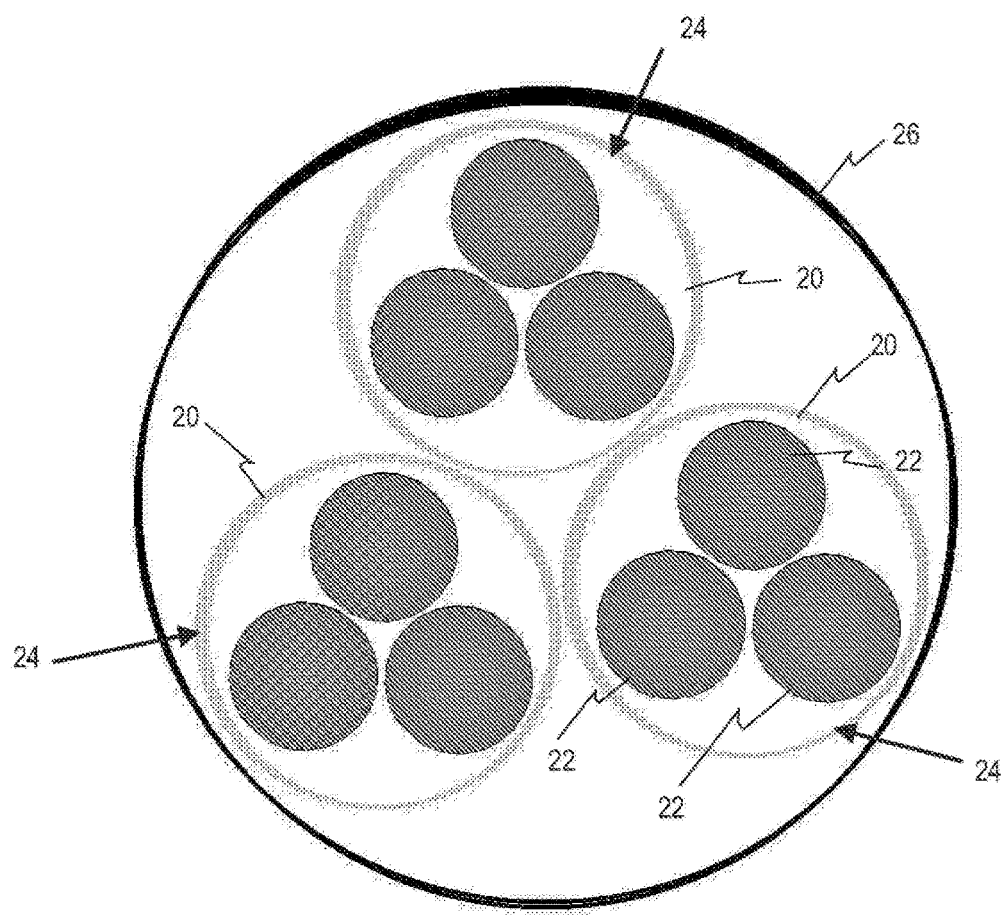
FIG. 8 is a cross-section of a three-group bionic muscle mass showing how the fiber, group mass and sheaths are arranged.

The bionic muscle mass is a grouping of three or more bionic muscle groups 24 (see FIG. 8) contained within an overall elastic non-electro-conductive sheath 26. This sheath is used to transfer contractive forces between muscle groups and to seal the muscle components from the external environment. The extension of the sheath at each end of the muscle mass forms the anchoring means (or tendons) for the bionic muscle mass.

The number of bionic muscle groups per bionic muscle masses is determined by the amount of contractive force required.

With the addition of an oil-based non electro conductive ferrofluid (i.e. a ferromagnetic liquid that is magnetizable in the presence of a magnetic field) performance of the bionic muscle mass may be enhanced. Without wishing to be limited by theory in any way it is proposed that the ferrofluid significantly enhances the electromagnetic efficiency of the electromagnetic fields generated at the cellular, fibre, group and muscle mass levels.

When used in conjunction with a means for circulating the ferrofluid through the muscle mass, the ferrofluid also acts to transport away any waste heat generated by the electrical and magnetic field resistance of the bionic muscle cells.

Additionally, the ferrofluid may (i) dampen the effect of muscle cells coming together, thereby creating a smoother and more natural contraction operation; (ii) inhibit oxidation of metallic materials within the muscle mass thereby extending the life of the muscle mass; (iii) act as a magnetic field shield around the muscle cell, minimising magnetic field interference from external magnetic fields.

Whilst the bionic muscle mass may be utilized to create an artificial skeletal muscle, the present invention is a universally applicable linear movement device and can be used to substitute any current movement device requiring linear rigid movement paths, as well as creating an industry to support the development of complex movement systems.

It should be appreciated that in the above description of exemplary embodiments of the invention, various features of the invention are sometimes grouped together in a single embodiment, figure, or description thereof, for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, components and functionality may be added or deleted from diagrams and operations may be interchanged among functional blocks. Steps may be added or deleted to methods described within the scope of the present invention.

The invention claimed is:

1. An electromagnetic device comprising:
a power circuit, and
a contact initiated electromagnet having a magnetic core and an electrical coil in operable connection with the power circuit,
wherein one end of the electrical coil is directly connected to the power circuit and the other end is connected to the magnetic core of the electromagnet such that, in use, the magnetic core performs the dual purposes of (i) focusing the electromagnetic field created by the coil and (ii) forming part of the electrical circuit that energizes the magnetic core of the electromagnet.

2. A kinetic device comprising two or more electromagnetic devices according to claim 1.

3. The kinetic device of claim 2 configured such that in use, when the electromagnet of a first electromagnetic device is energized, the magnetic field created magnetically attracts the electromagnet of an adjacent second electromagnetic device.

4. The kinetic device of claim 3 configured such that, in use, when the electromagnet of the second electromagnetic device makes electrical contact with the electromagnet of the first electromagnetic device, the electrical circuit for the electromagnet of the second electromagnetic device is closed and the electromagnet of the second electromagnetic device is energized to create a magnetic field.

5. The kinetic device of claim 2 wherein the two or more electromagnetic devices are disposed in series.

6. The kinetic device of claim 2 wherein the electrical coils of the two or more electromagnetic devices are electrically connected in parallel.

7. The kinetic device of claim 2 comprising a plurality of electromagnetic devices.

8. A system for simulating the function of a partial or complete mammalian muscle, the system comprising one or more kinetic devices according to claim 2, the one or more kinetic devices encased in a biocompatible material.

9. The system of claim 8 wherein the biocompatible material is elastic.

10. The system of claim 8 wherein the biocompatible material forms a bionic muscle fibre, the bionic muscle fibre containing a plurality of the kinetic devices.

11. The system of claim 10 wherein two or more electromagnetic devices within any one bionic muscle fibre are configured to be powered by the power circuit, wherein an amount of electrical energy applied is at least partially dependent on a mechanical force against which the system is operating.

12. The system of claim 10 configured such that adjacent kinetic devices form one or more points of contact along the long axes.

13. The system of claim 12 wherein the kinetic devices are configured such that the contact areas between two adjacent kinetic devices are maximized over a range of angular displacements between the magnetic axis of the adjacent kinetic devices.

14. The system of claim 10 wherein the electromagnetic devices within a kinetic device are, in their non-energized state, separated from one another along their magnetic axes by a distance that, when compared to the magnetic axial length of the kinetic device, creates a predetermined contraction ratio of the system when adjacent kinetic devices are in contact.

15. The system of claim 10 comprising three or more bionic muscle fibres configured to work mechanically in concert.

16. The system of claim 15 wherein the three or more bionic muscle fibres are encased by a biocompatible material to form a bionic muscle group.

17. The system of claim 16 wherein the biocompatible material is elastic.

18. The system of claim 16 wherein the bionic muscle fibres within a bionic muscle group are displaced relative to each other.

19. The system of claim 8 comprising a non-conductive ferromagnetic fluid, the fluid at least partially surrounding one, most or all of the kinetic devices.

20. A method of treating a muscle disorder in an animal, the method comprising the step of implanting the system of claim 8 into an animal, wherein the kinetic device or system is directly or indirectly mechanically coupled to a skeletal component of the animal.

21. The method of claim 20 wherein the system is directly or indirectly electrically coupled to a neural component of the animal.

\* \* \* \* \*